United States Patent
Romero et al.

(10) Patent No.: US 8,613,959 B2
(45) Date of Patent: Dec. 24, 2013

(54) DIETARY SUPPLEMENTS CONTAINING EXTRACTS OF NELUMBO AND PROCESSES OF USING SAME

(75) Inventors: Tim Romero, Sarasota, FL (US); Peter Miller, Broomfield, CO (US); Bolin Qin, Gaithersburg, MD (US)

(73) Assignee: FHG Corporation, Spring Hill, TN (US)

( * ) Notice: Subject to any disclaimer, the term of this patent is extended or adjusted under 35 U.S.C. 154(b) by 448 days.

(21) Appl. No.: 12/702,753

(22) Filed: Feb. 9, 2010

(65) Prior Publication Data
US 2010/0227007 A1    Sep. 9, 2010

Related U.S. Application Data

(60) Provisional application No. 61/151,380, filed on Feb. 10, 2009.

(51) Int. Cl.
*A61K 36/00* (2006.01)

(52) U.S. Cl.
USPC ......................................................... 424/725

(58) Field of Classification Search
None
See application file for complete search history.

(56) References Cited

U.S. PATENT DOCUMENTS

| | | | |
|---|---|---|---|
| 5,968,900 A | 10/1999 | Greenhaff et al. | |
| 2002/0098253 A1* | 7/2002 | Riley | 424/776 |
| 2007/0292403 A1* | 12/2007 | Nivaggioli | 424/94.1 |

FOREIGN PATENT DOCUMENTS

| | | | |
|---|---|---|---|
| CN | 101301083 A | * | 11/2008 |
| DE | 102006031441 A1 | * | 1/2008 |
| WO | 9800148 A1 | | 1/1998 |
| WO | 9838183 A1 | | 9/1998 |
| WO | 9843617 A2 | | 10/1998 |
| WO | 00/03604 A1 | | 1/2000 |

OTHER PUBLICATIONS

Steenge et al, Stimulatory effect of insulin on creatine accumulation in human skeletal muscle, Am J Phystol Endocrtnol Metab, 1998, 947-979, 275.

Mukherjee et al, Effect of *Melumbo nucifera* rhizome extract on blood sugar level in rats., J Ethnopharmacol, Nov. 1997, 207-213, 58(3).

Wyss M. et al, The therapeutic potential of oral creatine supplementation in muscle disease, Medical Hypothesis, 1998, 333-336, 51(4), United Kingdom.

Mahanna et al, Effects of .beta.-guanidinoprionic acid on murine skeletal muscle, Exp. Neurol, 1980, 114-121, 68 (1).

Smith et al, Creatine supplementation and age influence muscle metabolism during exercise, J. Appl. Physiol., 1998, 1349-1356, 85 (4).

Bermon et al, Effects of creatine monohydrate ingestion in sedentary and weight-trained older adults, ACTA Physiologica Scandanavica, Oct. 1998, 147-155, 164 (2), England, United Kingdom.

Heinanen et al, The effect of long-term creatine and guanidinoacetate supplementation on muscle 31phosphorus spectrum in HOGA, Journal of Inherited Metabolic Disease, 1997, pp. 23, vol. 20 No. Suppl. 1, Goteborg, Sweden.

Henriksson, Effect of training and nutrition on the development of skeletal muscle, Journal of Sports Sciences, 1995, S25-S30, vol. 13.

Zorzanzo et al, Biochem. J., 2000, 667-688, 349.

Juan et al, Olive Fruit Extracts Inhibit Proliferation and Induce Apoptosis in HT-29 Human Colon Cancer Cells, The Journal of Nutrition, 2006, 2553-2557, 136.

Harris et al, Glycogen, Glycolytic Intermediates and High-Energy Phosphates Determined in Biopsy Samples of Musculus Quadriceps Femoris of Man at Rest. Methods and Variance of Values, Scand. J. Clin. Lab. Invest., 1974, 109-120, 33(2).

Gennaro, Remington: The Science and Practice of Pharmacy, 20th Edition, 2003.

* cited by examiner

*Primary Examiner* — Terry McKelvey
*Assistant Examiner* — Randall Winston
(74) *Attorney, Agent, or Firm* — Gifford, Krass, Sprinkle, Anderson & Citkowski, P.C.; Weston R. Gould

(57) ABSTRACT

Materials derived from *Nelumbo* are administered orally to humans or animals for the purpose of enhancing creatine transport into skeletal tissue and for purposes of enhancing lean body mass. Enhancing creatine transport through improved insulin signaling is a new method of depositing creatine and enhancing lean body mass. Such administration is also used for enhancing athletic performance and controlling bodyweight and body fat levels. More specifically, such administration is used for the purpose of enhancing creatine transport into excitable tissues such as skeletal muscle. The material is administered as extracts of *Nelumbo* and administered in a variety of ways including capsules, tablets, powdered beverages, bars, gels or drinks.

24 Claims, No Drawings

DIETARY SUPPLEMENTS CONTAINING EXTRACTS OF NELUMBO AND PROCESSES OF USING SAME

CROSS REFERENCE TO RELATED APPLICATIONS

This application claims priority from U.S. Provisional Application No. 61/151,380 filed Feb. 10, 2009, the entire contents of which are in corporate herein by reference.

FIELD OF THE INVENTION

The present invention is directed to dietary supplements comprising *Nelumbo*, or extracts thereof, or derivatives of the extracts thereof, and creatine, or a derivative of creatine, or a precursor thereof, with or without a carbohydrate and to methods of using these dietary supplements to enhance creatine transport and to promote gains in lean body mass, both in humans and animals.

BACKGROUND

Enhancing muscle capacity and lean muscle mass is a primary goal of athletic training. The ability of skeletal muscle to deliver high output correlates with the amount of phosphocreatine stored in the tissue. The fuel for muscular work in the body is adenosine tri-phosphate, or ATP. During intense exercise ATP is utilized very rapidly. The body does not store much ATP in muscle, so other substances must be broken down in order to replenish ATP used during exercise. If the ATP is not replenished, fatigue occurs and force/power production declines. Of all the substances in the body that can replenish ATP, the fastest is phosphocreatine. Creatine kinase, the enzyme responsible for synthesizing phosphocreatine from creatine and ATP, is tightly regulated and highly responsive to levels of ATP and creatine in the muscle cell. Thus, upon ATP utilization during exercise the stored phosphate in phosphocreatine is rapidly converted to ATP for additional muscle capacity.

Creatine is a natural dietary component primarily found in animal products. In the body, creatine is stored predominantly in skeletal muscle, generally in the form of phosphocreatine. Total creatine content of mammalian skeletal muscle (i.e., creatine and phosphorylated creatine) typically varies from about 100 to about 140 mmol/kg. The level of creatine and phosphocreatine present in skeletal muscle can be increased through dietary supplementation with creatine.

Creatine is taken up into tissues, such as skeletal muscle, by means of an active transport system using the receptors CRT1 and CRT2. Zorzanzo, A, et al., Biochem. J., 2000; 349:667-688, the contents of which are incorporated herein by reference. Regulation of CRT1 and CRT2 are not fully elucidated. Some studies identified insulin as a possible regulator of creatine uptake. In a study by Stengee et al., insulin was co-infused along with creatine supplementation. (*Am. J. Physiol.*, 1998; 275:E974-79). Insulin was shown to enhance creatine accumulation in muscle, but only at extremely high or super-physiological concentrations. A previous study by Green et al. involved ingestion of creatine in combination with a carbohydrate-containing solution to increase muscular uptake of creatine by creating physiologically high plasma insulin concentrations. Green et al. reportedly found the quantity of carbohydrate necessary to produce a significant increase in creatine uptake, as compared to creatine supplementation alone, was close to the limit of palatability.

Insulin administration itself is also a detrimental method of improving creatine levels in muscle. Insulin has both positive and negative functions in human physiology. For example, insulin affects fat mass by enhancing the deposition of fatty acids leading to increased adiposity. For those seeking gains in lean body mass, fat mass is negatively correlated with physique enhancement.

Thus, a need exists for processes and compositions that promote improved creatine transport into muscle cells that are agreeable to the subject.

SUMMARY OF THE INVENTION

Disclosed herein is: (a) a dietary supplement comprising *Nelumbo*, or an extract thereof or a derivative of the extract thereof and a creatine, or a derivative or a precursor thereof, with or without a carbohydrate; and (b) methods of increasing the uptake of creatine in muscle, enhancing creatine transport, and promoting gains in lean body mass or muscle endurance comprising administration of said dietary supplement.

Accordingly, the invention provides processes and a dietary supplement to enhance the uptake of creatine into muscle. More specifically, the invention provides processes and a dietary supplement to enhance the uptake of creatine into skeletal muscle.

Also disclosed herein is: (a) a dietary supplement comprising *Nelumbo*, or an extract thereof or a derivative of the extract thereof and (b) methods of enhancing athletic performance, endurance, or recovery comprising administration of said dietary supplement.

DETAILED DESCRIPTION OF THE PREFERRED EMBODIMENTS

The invention provides methods and compositions for improving creatine levels in muscle cells. The invention has utility for altering or improving the levels of creatine or phosphocreatine in muscle cells to boost muscle cell activity or stamina. The invention also has utility for improving the rate of creatine uptake into muscle cells before, during, or after exercise.

The invention disclosed comprises *Nelumbo*, or an extract thereof or a derivative of the extract thereof and optionally a creatine, or a derivative or a precursor thereof, with or without a carbohydrate, and methods of increasing the uptake of creatine in mammalian muscle, enhancing creatine transport, or promoting gains in lean body mass comprising administration of an inventive dietary supplement.

In broad terms, creatine transport involves the deposit of creatine into various tissues by active transport of creatine across the plasma membrane from the blood through the activity of CRT1 and CRT2. Insulin has been indirectly implicated in altering the rate of creatine transport. Illustratively, U.S. Pat. No. 5,968,900 discloses methods by which insulin, either via exogenous infusion or via carbohydrate ingestion, may stimulate insulin levels for the purpose of enhancing creatine deposition into muscle cells.

Unexpectedly, the inventors discovered that the plant *Nelumbo nucifera* contains compounds that sufficiently alter insulin levels so as to stimulate creatine uptake by muscle cells in normal subjects when orally delivered along with creatine supplements. *Nelumbo* is a fairly common plant. *Nelumbo* is an aquatic perennial, but if its seeds are preserved under favorable circumstances they may remain viable for many years. *Nelumbo* was native to a huge area from modern Vietnam to Afghanistan, being spread widely as an ornamental and food plant. Today it is rare or extinct in the wild in Africa but widely naturalized in southern Asia and Australia where it is commonly cultivated in water gardens. The roots of *Nelumbo* are planted in the soil of a pond or river bottom, while the leaves float on top of the water surface. It grows in lakes and swamps, as well as areas subject to flooding.

Compounds present in *Nelumbo* illustratively include various saponins, flavonoids, quercetin, isoquercitin and many others. Flavonoids may be extracted from *Nelumbo* and isolated, and, optionally, derivatized. In some embodiments of the invention, the dietary supplement includes flavonoids.

The inventors found that the mRNA levels of the insulin signaling pathway components insulin receptor (IR), insulin receptor substrate 1 (IRS-1), insulin receptor substrate 2 (IRS-2), thymoma viral proto-oncogene 1 (Akt1), phosphatidylinositol 3-kinase, regulatory subunit 1 (PI3Kr1), and Src homology 2 domain-containing transforming protein 1 (SHC1) in the enterocytes of chow-fed hamsters were significantly enhanced by *Nelumbo*. Extracts of *Nelumbo* also inhibit SHC1 expression in these cells.

Additionally, IR, IRS-1, IRS-2, Akt1, PI3Kr1, and SHC1 in enterocytes of hamsters fed a high-fructose diet induce insulin resistance. *Nelumbo* extract significantly improves the impaired mRNA overexpression of IR, IRS-1, IRS-2, Akt1, and PI3Kr1, and inhibits SHC1 expression in enterocytes of these animals. Thus, the inventors identified a direct correlation between the mRNA levels for proteins involved in enhanced insulin signaling and *Nelumbo* extract administration.

An inventive composition and process of enhancing creatine uptake into muscle cells or improvement of lean muscle mass are provided. An inventive composition illustratively includes one or more portions of a *Nelumbo* plant, extracts of one or more portions of a *Nelumbo* plant, or a derivative of the extract of a *Nelumbo* plant optionally combined with creatine, a precursor of creatine, or a derivative of creatine.

The chemical name for creatine is methylguanidino acetic acid. The inventive compositions optionally include creatine or a derivative thereof, for example a hydrate, salt or ester thereof. Commercially available creatine derivatives include creatine monohydrate, other creatine hydrates, creatine citrate, and creatine pyruvate. The creatine which is employed in the compositions of the present invention optionally includes creatine monohydrate, commercially available from various sources. Optionally the creatine, creatine monohydrate or other creatine derivative is a pharmaceutical-grade material. Creatine derivatives illustratively include: creatine monohydrate and other hydrates; creatine salts such as creatine citrate; creatine esters; phosphorylated creatine; and creatine pyruvate. Creatine precursors illustratively include: glycocyamine; guanidineacetic acid; and the amino acids arginine, glycine, and methionine.

Specific illustrative examples of creatine derivatives include: creatine monohydrate; creatine anhydrous; creatine taurinate; creatine pyruvate; creatine ethyl ester; dicreatine malate; creatine deconate; creatine citrate; creatine phosphate; glycocyamine; creatine alpha ketogluturate; creatine ketoisocaproate; and creatine magnesium chelate. In some embodiments of the invention the dietary supplement includes creatine monohydrate.

The inventive composition optionally includes carbohydrate illustratively: simple sugars such as the monosaccharides glucose, fructose, ribose, mannose, galactose, dextrose, and the like; and complex sugars such as sucrose, maltose, cellobiose, lactose, raffinose, and the like. It is appreciated that larger polymers of monosaccharide units are similarly operable in the invention. Illustrative examples include amylase, amylopectin, cellulose, chitin, as well as heteromeric polysaccharides. In some embodiments saccharides are pharmaceutical grade. Sources for saccharides are well known in the art.

The amount of *Nelumbo, Nelumbo* extract, or derivative of *Nelumbo* extract in the inventive compositions is present in an amount sufficient to increase creatine transport into muscle cells when administered alone or with supplemental creatine, a creatine derivative, or creatine precursor. Typical formulations of compositions according to the invention illustratively include from about 1 mg to about 1000 mg of *Nelumbo, Nelumbo* extract, or derivative of a *Nelumbo* extract per gram. Inventive compositions optionally contain from about 100 mg to about 500 mg of creatine, creatine derivative, or creatine precursor per gram. In some embodiments carbohydrate is present from about 100 mg to about 900 mg of per gram of dietary supplement.

The compositions according to the present invention optionally include additional components to increase the rate or ease with which creatine enters the bloodstream and subsequently the muscle tissue, or to otherwise enhance the effects of the creatine in the body. Illustratively, additional amino acids are optionally included. Amino acids are optionally amino acid derivatives. Amino acids illustratively include glutamine, alanine, taurine, carnitine, acetyl-L-carnitine, and the like. These additional amino acids may stimulate cell volumization and protein synthesis and provide further advantages to increasing muscle strength and/or size. These amino acids are optionally employed individually or in various combinations and in amounts customary in the art, for example in the range of from about 0.01 mg to about 100 mg per gram of inventive composition.

The inventive compositions optionally include a chromium compound. Chromium is a constituent of a biologically active compound, the glucose tolerance factor (GTF), found in foods such as organ meats, whole grains, cheese, mushrooms and brewer's yeast. Various chromium compounds are optionally included in the inventive compositions, and in amounts effective to improve insulin efficiency. A preferred chromium compound is chromium picolinate, which is optionally present from about 50 micrograms to about 500 micrograms per 100 grams of supplement. Additional components for the inventive compositions illustratively include additional minerals such as magnesium, potassium, phosphorous, salts thereof, or mixtures thereof in amounts conventional in the art, for example, from about 0.01 mg to about 100 mg per gram of supplement. The inventive compositions optionally contain ascorbic acid (vitamin C), for example in amounts equal to or exceeding the recommended minimum daily requirements. Optionally included is beta-hydroxy, beta-methyl butyrate (HMB), in amounts known in the art.

Optionally, the inventive composition is combined with one or more protein sources. Such sources may include whey protein isolate, whey protein concentrate, free form amino acids, buckwheat protein, soy protein isolate or concentrate, milk protein isolate or concentrate, micellar casein, calcium or other caseinate proteins, rice protein, or any combination of the above. Optionally, the protein contains quantities of essential amino acids.

Also, provided are processes of increasing the level of creatine in skeletal muscle or muscle cells by administration of an inventive composition to a subject. A subject is optionally a patient. A subject is optionally a mammal such as humans, non-human primates, horses, goats, cows, sheep, pigs, dogs, cats, and rodents. A subject is optionally an athlete.

An inventive process is optionally used to supplement the diet of a subject, to enhance or increase muscle, optionally lean muscle, or muscle strength or endurance. Inventive processes illustratively enhance the anabolic environment for obtaining increased lean muscle mass or strength.

It is contemplated that variable dosing regiments are operative in the inventive processes. While in some instances a single dose of inventive composition as a dietary supplement, for example, may be effective in producing therapeutic effects, in other instances a treatment period in the range of, for example, 6 weeks to 3 months may be utilized. An inventive composition is optionally delivered to a subject daily, weekly, biweekly, monthly, or any subdivision therebetween or for longer periods. In some embodiments a subject ingests an inventive composition daily. Optionally, an inventive composition is delivered one, two, three, four, five, or more times per day.

The composition is optionally administered orally, parentally, or intravenously by intramuscular, intraperitoneal, or transdermally injection. Injectables may be prepared in conventional forms, either liquid solutions or suspensions, solid forms suitable for solution or prior to injection, or as suspension in liquid prior to injection or as emulsions. The dose of the dietary supplement composition may vary depending on the age, weight, general condition of the user. Several forms of administration are operable herein illustratively including ingestion, inhalation, or injection. Typical administrations are by oral ingestion. Ingestion is optionally with or without other food. In some embodiments an inventive composition is administered to a subject along with a carbohydrate rich food or within 1 hour prior or following administration illustratively by eating a carbohydrate rich food. Carbohydrate rich foods are foods that in ingestible quantities include greater than about 50 mg of carbohydrate. More preferably, a carbohydrate rich food contains greater than about 100 mg, 200 mg, 300 mg, 400 mg, 500 mg, 1000 mg, 5000 mg, 10,000 mg, or more carbohydrate per serving.

The amount of the inventive composition administered to the diet or otherwise of a subject varies depending on the desired effect, the body weight and characteristics of the subject, and the like. Those of ordinary skill in the art recognize methods of administration for particular desired outcomes. Typical dosages of the inventive composition are about 10 mg to about 1,000 mg of *Nelumbo, Nelumbo* extract, or a *Nelumbo* extract derivative and optionally about 1 g to about 50 g of creatine, creatine derivative, or creatine precursor. In some embodiments a dosage includes from about 2 g to about 25 g of creatine, creatine derivative, creatine precursor. In some embodiments where an inventive composition includes creatine, a creatine derivative, or a creatine precursor a loading dose is used. A loading dose illustratively includes about 20-25 grams of creatine, a creatine derivative, or a creatine precursor administered daily for 5 days, This is optionally followed by a steady maintenance dose of creatine, a creatine derivative, or a creatine precursor from about 2-10 grams per day.

Typical dosages of the inventive composition are from about 10 mg to about 1,000 mg of *Nelumbo, Nelumbo* extract, or *Nelumbo* extract derivative. In some embodiments, *Nelumbo, Nelumbo* extract, or *Nelumbo* extract derivative are administered in an amount from about 250 mg to about 1,000 mg.

In some embodiments of the inventive processes, greater amounts of the inventive composition are initially administered to the subject's diet in order to increase or enhance muscle size or strength (loading period), followed by a maintenance period during which the amounts of inventive composition are relatively decreased. The loading period optionally extends several weeks. In some embodiments a loading period is one, two, three, four, five, six or more weeks. Optionally, a loading period is from one day to six weeks or more, as well as any period therebetween as desired by either the subject, the trainer, physician, or other depending on the desired outcome and rapidity of desired results. Once a desired muscle strength, size, or endurance has been obtained, lower amounts of the inventive composition, illustratively a maintenance period, are optionally administered to the subject to maintain or improve the results. In some embodiments the inventive composition is administered to a subject immediately following an exercise period. On non-workout days, the inventive composition is optionally administered anytime during the day, illustratively, upon awakening or otherwise during the morning hours.

In some embodiments an inventive composition includes other compounds to further enhance creatine levels in cells. Such compounds illustratively include: cinnamon extracts, alpha lipoic acid, corosolic acid, banaba, coccinia indica, momordica, D-pinitol, vanadium, chromium, cecropia, amino acids, and the like.

Depending on the intended mode of administration, the inventive composition is present in pharmaceutical compositions in the form of solid, semi-solid, or liquid dosage forms, illustratively tablets, suppositories, pills, capsules, powders, liquids, or suspensions, and are optionally provided in unit dosages suitable for a single administration. Time release preparations are specifically contemplated as effective dosage formulations. Methods for creating time release preparations are known in the art. The compositions optionally include a desired amount of the selected *Nelumbo* preparation in combination with a pharmaceutically acceptable carrier and, in addition, optionally include other medicinal agents, pharmaceutical agents, carriers, or diluents.

The inventive compositions are optionally mixed with various food items such as water, fruit juice, milk, cereal, or other food and simultaneously consumed therewith.

The dietary supplements of the invention are optionally orally administered such as in the form of capsules, tablets, powdered beverages, bars, gels or drinks. For oral administration, fine powders or granules optionally contain diluting, dispersing, and/or surface active agents, and are optionally presented in water or in a syrup, in capsules or sachets in the dry state or in a non-aqueous solution or suspension wherein suspending agents may be included, in tablets wherein binders and lubricants may be included, or in a suspension. Where desirable or necessary flavoring, preserving, suspending, thickening, or emulsifying agents may be included. Tablets and granules are commonly oral administration forms, and these are optionally coated for ease of digestion, storage, stability or other purpose.

For solid compositions, conventional nontoxic solid carriers include, for example, pharmaceutical grades of mannitol, lactose, starch, magnesium stearate, sodium saccharine, talc, cellulose, glucose, sucrose, and magnesium carbonate. Liquid pharmaceutically administrable compositions can, for example, be prepared by dissolving or dispersing a *Nelumbo* preparation with optimal pharmaceutical adjuvants in an excipient, such as water, saline, aqueous dextrose, glycerol, or ethanol, to thereby form a solution or suspension. If desired, the pharmaceutical composition to be administered optionally contains minor amounts of nontoxic auxiliary substances such as wetting or emulsifying agents, pH buffering agents, for example, sodium acetate or triethanolamine oleate. Actual methods of preparing such dosage forms are known, or will be apparent, to those skilled in this art; for example, see Remington's The Science and Practice of Pharmacy (20th Edition), the contents of which are incorporated herein by reference.

The increase in the amount of creatine storage in muscle is optionally measured by muscle biopsy. Upon administration of the inventive composition for a period of days, illustratively for as little as 4 days, and as many as 30 days or more, the total creatine content of skeletal muscle (i.e., free and phosphorylated creatine) will increase from about 10% to about 40% where typical levels of total creatine in skeletal muscle prior to administration are between about 100 to about 140 mmol/kg of dry muscle.

Extracts are prepared by various methods. Extraction parameters such as water quality, heating temperature, drying temperature, heating time, drying time, and filtering processes all contribute to the quality and efficiency of the process. Water quality directly affects the concentration of active compounds. Poor quality water may cause active ingredients to become decomposed and oxidized during the extraction process. Extracts are optionally prepared with ethanol or other organic solvent. In some embodiments, the plant material undergoes both aqueous and solvent extraction. The process is similar to that of an aqueous extraction except illustratively with a ratio 70:30 alcohol:water. Other ratios such as 50:50, more or less relative water or organic solvent are also operable. This may in fact increase the yield output, particularly of the flavonoid concentration.

Regardless of the natural source location or portion of the *Nelumbo* plant, the inventive compositions are optionally extracted with polar aprotic solvents such as methylene chloride, C1-C6 alcohols, C3-C6 ketones, tetrahydrofuran, formamid, C3-C16 esters, nitrogen-containing heterocyclics, and combinations thereof. In particular, it is appreciated that crude extraction from macerated plant material in a first solvent followed by a secondary extraction from the inventive acid-containing fraction serves to further purify the inventive materials. A water or methylene chloride initial extraction followed by a methanol or ethanol extraction is exemplary of such extraction processes (Juan et al., *J. Nutri.*, 136, p. 2554, first column, ¶¶1-2, 2006).

Heating time affects the level of active component and also affects the thickness of extraction mixture which then has a direct impact on the downstream filtering process. Lastly, drying temperature optionally varies from 75° C. to 120° C., optionally from 50° C. to 120° C., depending on what other extraction parameters are also used. Drying is appreciated to be operable at ambient temperature.

In one embodiment, 50 g clean leaf of the *Nelumbo nucifera* plant is ground into small particles or powder. The powder or particles are mixed with 1000 ml distilled water in a suitable flask. The mixture is let stand at room temperature for about 0.5 hour. Additional water may be added is in the range of 1:20 to 1:2000. Too little water may render the mixture too thick for extraction. However, too much water increases drying time. Then the water mixture is heated while being stirred through the use of a magnetic heat stirrer. The temperature and extraction time are crucial to the concentration efficiency of the extract. The extraction process is optionally no longer than one hour. In some embodiments the ground plant material is heated for 15-20 minutes bringing to a boil, simmering for 20-30 minutes optionally while stirring constantly. The boiling time is typically controlled at about 20-25 minutes following heating. The mixture is optionally cooled and stored at 4° C. overnight.

In other embodiments, the extraction solution is filtered through a filter paper to remove any solid debris. If the solution is too thick for the filter paper, the removal of solids from the solution is optionally done with the use of centrifugation. The resulting supernatant is optionally filtered through medium speed filter paper. The resulting solids are optionally dissolved in 200 mL distilled water for a second extraction. The liquid solution containing the solids is mixed and heated for 30 minutes at 50-100° C., optionally 80-90° C., and then is filtered.

In other embodiments, the first and second extraction solutions are combined together and poured onto nonstick tray and allowed to dry at 50-100° C., optionally 80-90° C. Vacuum-spray dry equipment is optionally used for the drying procedure. The resulting dry extract powder is weighed. An extraction ratio is calculated as w/20×100% with w as the weight (g) of the dry powder. The sample and water ratio, heat time, volume of water in the second extraction may vary depending on the amount of the raw material used for extraction.

One aspect of the inventive compositions is their ability to promote increased lean muscle mass or improved muscle performance. Muscle performance is illustratively measured by a subject's improved exercise endurance, muscle energy output, or strength. Additional measurements include decreased recovery time. Cellular endpoints illustratively include increased creatine levels, improved insulin sensitivity, enhanced glucose tolerance, increased levels of ion dependent active transport, increased Glut4 activity, increased CRT1 or CRT2 activity, increased levels of resting ATP, or combinations thereof. Methods of measuring each of the herein presented parameters are known in the art.

Administration of the dietary supplements of the invention, particularly to individuals with impaired glucose tolerance, will have the effect of restoring optimal glucose functioning, therefore lessening the likelihood of adipose storage, and leading to a reduction in body fat and weight.

Various aspects of the present invention are illustrated by the following non-limiting examples. The examples are for illustrative purposes and are not a limitation on any practice of the present invention. It will be understood that variations and modifications can be made without departing from the spirit and scope of the invention. One of ordinary skill in the art readily knows how to synthesize or commercially obtain the reagents and components described herein.

Example 1

50 g clean leaf of the *Nelumbo nucifera* plant is ground into small particles or powder. The powder or particles are mixed with 1000 ml (10 volumes) distilled hot water (90° C.) in a suitable flask. The mixture is let stand at room temperature for about 60 minutes. The extracted material is centrifuged to remove insoluble matter. The extraction solution is poured onto nonstick tray and dried at 85° C. The resulting dry material is stored at 4° C.

The extract of Formula A is prepared to include the above extract and the following ingredients to create a dietary supplement of Formula A.

Formula A

| Component | grams |
|---|---|
| Dextrose | 25 |
| Creatine Blend | |
| Creatine Monohydrate | 6 |
| Creatine Anydrous | 0.5 |

-continued

| Component | grams |
|---|---|
| Creatine AKG | 0.5 |
| DiCreatine Malate | 0.5 |
| Creatinie Gluconate | 0.5 |
| Creatinol-O-Phophate | 0.01 |
| Insulin/Volume | |
| Chromium | 0.0005 |
| Cinnulin PF | 0.125 |
| Nelumbo extract | 0.25 |
| Glutamine AKG | 0.25 |
| Potassium Phosphate | 0.1 |
| Magnesium Phosphate | 0.1 |
| Sodium Phosphate | 0.1 |
| Flavor System | |
| Citric Acid | 0.05 |
| Malic Acid | 0.05 |
| Natural Flavors | 2.5 |
| Color | 0.01 |
| Sucralose | 0.05 |
| Acesulfame Potassium | 0.025 |
| Total Weight | 36.6205 |

Example 2

The *Nelumbo* extract of Example 1 is used with supplemental materials to make a dietary supplement of Formula B.
Formula B:

| Component | g |
|---|---|
| Creatine Blend | |
| Creatine Pyruvate | 3 |
| Creatine Ethyl Ester | 0.5 |
| DiCreatine Malate | 0.5 |
| Creatinie Gluconate | 0.5 |
| Glycocyamine | 0.01 |
| Creatine Transport Enhancement | |
| Nelumbo extract | 0.5 |
| Flavor System | |
| Citric Acid | 0.03 |
| Malic Acid | 0.02 |
| Natural Flavors | 0.8 |
| Color | 0.01 |
| Sucralose | 0.05 |
| Acesulfame Potassium | 0.025 |
| Total Weight | 5.945 |

Example 3

The extract of example 1 is used to make a dietary supplement of Formula C in the form of a capsule for oral administration.
Formula C:

| Creatine Monohydrate | 0.5 |
|---|---|
| Nelumbo extract | 0.25 |
| Total Weight | 0.75 |

Example 4

Twenty consenting athletes consume two servings of the composition of Formula A daily, one in the morning and the other twelve hours later or immediately after exercise. This regime is continued for five days. Prior to and at the end of the five day period the subjects are subjected to treadmill stress test to measure muscle stamina. At the end of the test period the subjects report improved stamina.

Example 5

Twenty consenting subjects take two daily doses of the composition of Formula C for a period of four weeks. Prior to the test period and after the test period the subjects perform a free weight repetition test. Each subject is asked to raise a 30 pound weight from the floor to a five foot mark. The number of repetitions relates to the level of muscle stamina. At the end of the test period the average number of repetitions is increased by five percent.

Example 6

The inventive composition of Formula C is administered in a double-blind study to a group of 6 body builders, with 4 body builders acting as negative controls. Each subject consumed a diet composed of between 25 and 30 total weight percent protein with the controls receiving the composition provided in Formula C with the exception of the *Nelumbo* extract. The compositions are administered once daily for 6 weeks. The test subjects at the end of the trial show a 2% increase in lean body mass relative to the control group.

Example 7

The trial of Example 6 is repeated with the inventive composition of Formula A substituted for that of Formula C while a repeat study control group received the Formula A formulation lacking *Nelumbo* extract with a comparable result to that of Example 6.

Example 8

The procedure of Example 6 is repeated with the composition taken orally within 2 hours of completing the most strenuous exercise routine of the day with comparable results to that of Example 6.

Example 9

Measuring creatine levels of creatine in muscle cells. Creatine measurements are performed essentially described in WO 2000/03604A1, the contents of which are incorporated herein by reference. Biochemical and histochemical analyses muscle samples for biochemical determinations are freeze-dried and washed twice in petroleum ether to remove fat. Thereafter a portion of each sample is dissected free of visible blood and connective tissue is pulverized. The powdered extract is then used for spectrophotometric determination of glycogen, free creatine and phosphocreatine concentration essentially as described by Harris, R. C. et al., *Scand. J. Clin. Lab. Invest.*, 33; 109-120:1974, the contents of which are incorporated herein by reference.

Various modifications of the present invention, in addition to those shown and described herein, will be apparent to those skilled in the art of the above description. Such modifications are also intended to fall within the scope of the appended claims.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A composition for increasing creatine levels in muscle comprising:
   a water extract of *Nelumbo*, or a water extract of a derivative of *Nelumbo*, said water extract of *Nelumbo* prepared by a process comprising a first extraction, said first extraction in an extraction solvent consisting of water; and
   creatine, a creatine derivative, or a creatine precursor.

2. The composition of claim 1 wherein said *Nelumbo*, *Nelumbo* extract, or a derivative of *Nelumbo* extract is a *Nelumbo* water extract.

3. The composition of claim 2 wherein said *Nelumbo* extract is present from about 10 milligrams to about 1,000 milligrams.

4. The composition of claim 1 wherein said creatine, creatine derivative, or creatine precursor is creatine monohydrate present from about 2 grams to 25 grams.

5. The composition of claim 1 wherein said extract consists essentially of *Nelumbo* extract and creatine monohydrate.

6. The composition of claim 5 wherein said *Nelumbo* extract is present from about 10 milligrams to about 1,000 milligrams and said creatine, creatine derivative, or creatine precursor is creatine monohydrate present from about 2 grams to 25 grams.

7. A process of increasing the level of total creatine in a muscle cell of a subject comprising:
   administering to said subject the composition of claim 1.

8. The process of claim 7 wherein said composition is made by extracting ground *Nelumbo* plant in water; and
   measuring the level of creatine in said muscle.

9. The process of claim 7 wherein said composition is administered daily.

10. The process of claim 7 wherein said composition is administered daily for four to six weeks.

11. The process of claim 7 wherein said composition is administered more than one time per day.

12. A process of increasing muscle endurance in a subject comprising:
    administering to said subject the composition of claim 1.

13. The process of claim 12 wherein said composition is administered daily.

14. The process of claim 12 wherein said muscle endurance is measured by repetitive weight lifting.

15. The process of claim 12 wherein said extract consists essentially of *Nelumbo* extract and creatine monohydrate.

16. The process of claim 15 wherein said *Nelumbo* extract is present from about 10 milligrams to about 1,000 milligrams and said creatine is creatine monohydrate present from about 2 grams to 25 grams.

17. The process of claim 12 wherein said dietary supplement consists essentially of a water extract of *Nelumbo* wherein said extract is made by extracting ground *Nelumbo* plant in water at a temperature from about 50 degrees Celsius to 100 degrees Celsius; and
    creatine monohydrate.

18. The process of claim 12 wherein said dietary supplement is added to a liquid.

19. The process of claim 12 wherein said dietary supplement is administered to a subject for a one week loading period followed by a three to five week maintenance period.

20. A process of for increasing lean muscle mass without increasing adiposity in a mammalian subject comprising:
    administering to said subject the composition of claim 1.

21. The process of claim 20 wherein said dietary supplement is administered orally.

22. The process of claim 20 wherein said dietary supplement contains at least 10 milligrams *Nelumbo* water extract per serving.

23. The process of claim 20 wherein said dietary supplement is taken orally within two hours of strenuous exercise.

24. A composition for increasing creatine levels in muscle comprising:
    an extract of *Nelumbo*, or a derivative of *Nelumbo*, said extract of *Nelumbo* comprising the supernatant material from a first extraction step; and
    creatine, a creatine derivative, or a creatine precursor.

* * * * *